United States Patent
Sherman et al.

(10) Patent No.: US 10,166,071 B2
(45) Date of Patent: *Jan. 1, 2019

(54) MULTI FREQUENCY AND MULTI POLARITY COMPLEX IMPEDANCE MEASUREMENTS TO ASSESS ABLATION LESIONS

(71) Applicant: Medtronic Ablation Frontiers LLC, Minneapolis, MN (US)

(72) Inventors: Marshall L. Sherman, Cardiff by the Sea, CA (US); Catherine R. Condie, Shoreview, MN (US); Mark T. Stewart, Lino Lakes, MN (US)

(73) Assignee: Medtronic Ablation Frontiers LLC, Minneapolis, MN (US)

( * ) Notice: Subject to any disclaimer, the term of this patent is extended or adjusted under 35 U.S.C. 154(b) by 340 days.

This patent is subject to a terminal disclaimer.

(21) Appl. No.: 14/996,875

(22) Filed: Jan. 15, 2016

(65) Prior Publication Data

US 2016/0128603 A1 May 12, 2016

Related U.S. Application Data

(63) Continuation of application No. 13/017,122, filed on Jan. 31, 2011, now Pat. No. 9,265,557.

(51) Int. Cl.
*A61B 18/14* (2006.01)
*A61B 18/02* (2006.01)
(Continued)

(52) U.S. Cl.
CPC ........ *A61B 18/1492* (2013.01); *A61B 5/4848* (2013.01); *A61B 18/02* (2013.01);
(Continued)

(58) Field of Classification Search
CPC ..... A61B 18/02; A61B 18/12; A61B 18/1492; A61B 2018/00869; A61B 2018/00666;
(Continued)

(56) References Cited

U.S. PATENT DOCUMENTS

| | | | |
|---|---|---|---|
| 6,066,139 A | 5/2000 | Ryan et al. | |
| 6,123,702 A | 9/2000 | Swanson et al. | |

(Continued)

FOREIGN PATENT DOCUMENTS

| | | |
|---|---|---|
| CN | 101534736 A | 9/2009 |
| WO | 2007005976 A1 | 1/2007 |

OTHER PUBLICATIONS

The State Intellectual Property Office of the People's Republic of China, Notice on the First Office Action and Search Report, Application/Patent No. 201280006887.4, Applicant: Medtronic Ablation Frontiers LLC, Title: Multi Frequency and Multi Polarity Complex Impedance Measurements to Assess Ablation Lesions, dated Apr. 9, 2015, 14 pages.

(Continued)

*Primary Examiner* — Eunhwa Kim
(74) *Attorney, Agent, or Firm* — Christopher & Weisberg, P.A.

(57) ABSTRACT

A method of assessing a tissue ablation treatment, including positioning a medical device adjacent a target tissue; measuring a first impedance magnitude a first frequency with the medical device; measuring a first impedance phase at a second frequency with the medical device; ablating at least a portion of the target tissue with the medical device; measuring at second impedance magnitude at a third frequency with the medical device; measuring a second impedance phase at a fourth frequency with the medical device; comparing at least one of (i) the first and second impedance magnitudes and (ii) the first and second impedance phases;

(Continued)

and providing an indication of the efficacy of the ablation treatment based at least in part on the comparison.

20 Claims, 12 Drawing Sheets

(51) Int. Cl.
   *A61B 18/12* (2006.01)
   *A61B 5/00* (2006.01)
   *A61B 17/00* (2006.01)
   *A61B 18/00* (2006.01)

(52) U.S. Cl.
   CPC .... *A61B 18/12* (2013.01); *A61B 2017/00128* (2013.01); *A61B 2018/0016* (2013.01); *A61B 2018/0022* (2013.01); *A61B 2018/00214* (2013.01); *A61B 2018/00267* (2013.01); *A61B 2018/00279* (2013.01); *A61B 2018/00285* (2013.01); *A61B 2018/00404* (2013.01); *A61B 2018/00577* (2013.01); *A61B 2018/00642* (2013.01); *A61B 2018/00648* (2013.01); *A61B 2018/00666* (2013.01); *A61B 2018/00869* (2013.01); *A61B 2018/00875* (2013.01); *A61B 2018/0212* (2013.01)

(58) Field of Classification Search
   CPC ........... A61B 2018/00648; A61B 2018/00642; A61B 2018/00577; A61B 2018/00267; A61B 2018/0022; A61B 2018/00214; A61B 2018/0016; A61B 2018/0212; A61B 2018/00875; A61B 2018/00285; A61B 2018/00279; A61B 2018/00404; A61B 5/0531; A61B 5/0536; A61B 5/4848; A61B 5/7246
   See application file for complete search history.

(56) References Cited

U.S. PATENT DOCUMENTS

| | | |
|---|---|---|
| 6,186,147 B1 | 2/2001 | Cobb |
| 6,391,024 B1 | 5/2002 | Sun et al. |
| 6,582,425 B2 | 6/2003 | Simpson |
| 7,184,820 B2 | 2/2007 | Jersey-Willuhn et al. |
| 7,344,533 B2 | 3/2008 | Pearson et al. |
| 7,419,487 B2 | 9/2008 | Johnson et al. |
| 8,257,303 B2 | 9/2012 | Moll et al. |
| 2002/0068931 A1 | 6/2002 | Wong et al. |
| 2006/0235286 A1 | 10/2006 | Stone et al. |
| 2007/0270795 A1 | 11/2007 | Francischelli et al. |
| 2008/0009764 A1 | 1/2008 | Davies |
| 2009/0030477 A1 | 1/2009 | Jarrard |
| 2009/0182318 A1 | 7/2009 | Abboud et al. |
| 2009/0306643 A1 | 12/2009 | Pappone et al. |
| 2010/0179538 A1 | 7/2010 | Podhajsky |

OTHER PUBLICATIONS

Bosnos et al., Early Assessment of Biophysical Parameters Predicts Lesion formation during RF Energy Delivery in Vitro, Sarver Heart Center, University of Arizona, Arizona Cancer Center, and Bard Electrophysiology Division, Lowell, Massachusetts, Feb. 23, 2010, pp. 1-7.

Hope et al., Technology Review: The use of electrical impedance scanning in the detection of breast cancer, Breast Cancer Res, 2004, vol. 6, pp. 69-74.

Piorkowski et al., First in Human Validation of Impedance-Based Catheter Tip-to-Tissue Contact Assessment in the Left Atrium, J. Cardiovasc Electrophysiol, vol. 20, pp. 1366-1373, Dec. 2009.

He, Ding Sheng et al., Assessment of Myocardial Lesion Size During In Vitro Radio Frequency Catheter Ablation, IEEE Transactions on Biomedical Engineering, vol. 50, No. 6, pp. 768-775, Jun. 2003.

MULTI FREQUENCY AND MULTI POLARITY COMPLEX IMPEDANCE MEASUREMENTS TO ASSESS ABLATION LESIONS

CROSS-REFERENCE TO RELATED APPLICATION

This application is a continuation of patent application Ser. No. 13/017,122, filed Jan. 31, 2011, entitled MULTI FREQUENCY AND MULTI POLARITY COMPLEX IMPEDANCE MEASUREMENTS TO ASSESS ABLATION LESIONS, the entirety of which is incorporated herein by reference.

STATEMENT REGARDING FEDERALLY SPONSORED RESEARCH OR DEVELOPMENT n/a

FIELD OF THE INVENTION

The present invention relates to a method and system for treating tissue, and more particularly, towards a system and method of use thereof for assessing the efficacy of a treatment procedure.

BACKGROUND OF THE INVENTION

Radiofrequency (RF) and cryogenic ablation procedures are well recognized treatments for vascular and cardiac diseases such as atrial fibrillation. The application of either RF or cryogenic treatment is usually based on the preference of the surgeon or the specific tissue to be treated. In either RF or cryogenic ablation, however, the location and quality of the lesion produced is a primary concern. The clinical success of cardiac tissue ablation to treat arrhythmias depends on efficacy and safety of the application of the selected energy. Many factors influence lesion size such as tissue-electrode contact force, ablation energy level, and cooling factors, that is, blood flow rate, tissue perfusion, and the duration of energy delivery. In addition, there are other factors that can limit deep lesion formation, such as early impedance rise that prevents continued energy delivery. Predicting and assessing lesion size and quality is important to the success of the ablation, but it has been difficult to achieve.

Current methods to identify a lesion's location and assess its quality include coupling a plurality of electrodes to the distal end of a medical device proximate a tissue to be treated, applying a voltage, and measuring impedance across the electrodes with the tissue to be treated completing the circuit. Electrical impedance is defined as the total opposition to alternating current by an electric circuit, equal to the square root of the sum of the squares of the resistance and reactance of the circuit and usually expressed in ohms. In general, the impedance decreases as cell membranes become ruptured and cellular fluids are released into the extracellular space in the regions of treated tissue. These treated regions then become necrotic. As such, impedance may be used to identify particular areas which have been treated and those that have not. It also should be noted that when sufficiently high voltage is applied to tissues, cells may undergo irreversible electroporation which creates permanent pores in the treated cell membranes. This process also releases fluids into the extracellular spaces and leads to tissue necrosis as do the RF and cryogenic therapies.

One drawback to impedance tomography is its lack of direct feedback to evaluate whether a lesion was successfully created to the desired transmurality, quality, or continuity. In particular, impedance measurements provide binary data regarding a particular lesion; either the tissue is viable or necrotic. Impedance measurements alone, however, do not provide real-time assessment of whether a cryogenic or RF lesion was successfully created to a desired lesion depth, in part, because different tissue levels have different impedances.

Tissue ablation technology often utilizes catheter tip temperature monitoring with feedback control to titrate energy delivery. The major limitation of this approach is that the catheter tip temperature and tissue temperatures are not the same. The catheter tip temperature is consistently lower than tissue temperature. The difference is variable and is dependent on the force of the catheter tissue contact that determines impedance as well as cooling of the catheter tip.

In view of the above, it would be desirable to provide improved methods of assessing tissue contact, lesion quality and depth, and other characteristics of cryogenically and/or RF treated tissue to determine the efficacy and resulting characteristics of the treatment.

SUMMARY OF THE INVENTION

The present invention advantageously provides a method and system for assessing tissue contact, lesion quality and depth, and other characteristics of cryogenically and/or RF treated tissue to determine the efficacy and resulting characteristics of the treatment. In particular, a method of assessing an efficacy of a medical treatment is provided, including positioning a medical device proximate a tissue site; obtaining baseline impedance characteristics at a first plurality of frequencies with the medical device; treating the tissue site; obtaining post-treatment impedance characteristics at a second plurality of frequencies with the medical device; comparing the post-treatment impedance characteristics and the baseline impedance characteristics; and generating an indication of the efficacy of the treatment base at least in part on the comparison. The baseline impedance characteristics and the post-treatment impedance characteristics may each include an impedance magnitude, and the comparison may include calculating a percentage difference between the baseline and post-treatment impedance magnitudes. The baseline impedance characteristics and the post-treatment impedance characteristics may each include an impedance phase, and the comparison may include calculating a percentage difference between the baseline and post-treatment impedance phases. The first plurality of frequencies may be substantially the same as the second plurality of frequencies.

A method of assessing a tissue ablation treatment is provided, including positioning a medical device adjacent a target tissue; measuring a first impedance magnitude a first frequency with the medical device; measuring a first impedance phase at a second frequency with the medical device; ablating at least a portion of the target tissue with the medical device; measuring at second impedance magnitude at a third frequency with the medical device; measuring a second impedance phase at a fourth frequency with the medical device; comparing at least one of (i) the first and second impedance magnitudes and (ii) the first and second impedance phases; and providing an indication of the efficacy of the ablation treatment based at least in part on the comparison. Ablating the tissue may include the application of at least one of cryogenic energy, radiofrequency energy and pulsed high voltage energy with the medical device. The first frequency and the third frequency may be substantially the same; the second frequency and the fourth frequency may be substantially the same; the first frequency and the third frequency may each be approximately 10 kHz or less; the second frequency and the fourth frequency may each be approximately 200 kHz or more; and/or the second frequency and the fourth frequency may each be larger than the first and third frequencies. Comparing at least one of (i) the first and second impedance magnitudes and (ii) the first and second impedance phases may include calculating a percentage difference between the compared measurements. The method may include measuring a plurality of impedance magnitudes during the ablation; and calculating a rate of change of the measured impedance magnitudes. The method may also include measuring a plurality of impedance phases during the ablation; and calculating a rate of change of the measured impedance phases. The method may include measuring at least one of a plurality of impedance phases and a plurality of impedance magnitudes at a first frequency during the ablation; calculating a rate of change of the measured impedance phases or impedance magnitudes at the first frequency; measuring at least one of a plurality of impedance phases and a plurality of impedance magnitudes at a second frequency during the ablation; and calculating a rate of change of the measured impedance phases or impedance magnitudes at the second frequency; where the indication of the efficacy of the ablation treatment is based at least in part on the calculated rates of change at the first and second frequencies.

A method of assessing a tissue ablation treatment is provided, including positioning a medical device adjacent a target tissue; creating an ablative lesion on at least a portion of the target tissue with the medical device; measuring a first impedance characteristic between at least two electrodes on the medical device; measuring a second impedance characteristic between at least one electrode on the medical device and an electrode remote from the medical device; generating an indication of a continuity of the lesion based at least in part on the first impedance characteristic; and generating an indication of a depth of the lesion based at least in part on the second impedance characteristic. The method may include defining an impedance characteristic threshold, and comparing at least one of the measured first and second impedance characteristics to the threshold. At least one of the measured first and second impedance characteristics may include an impedance phase and/or an impedance magnitude.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION OF THE INVENTION

Figure 1:
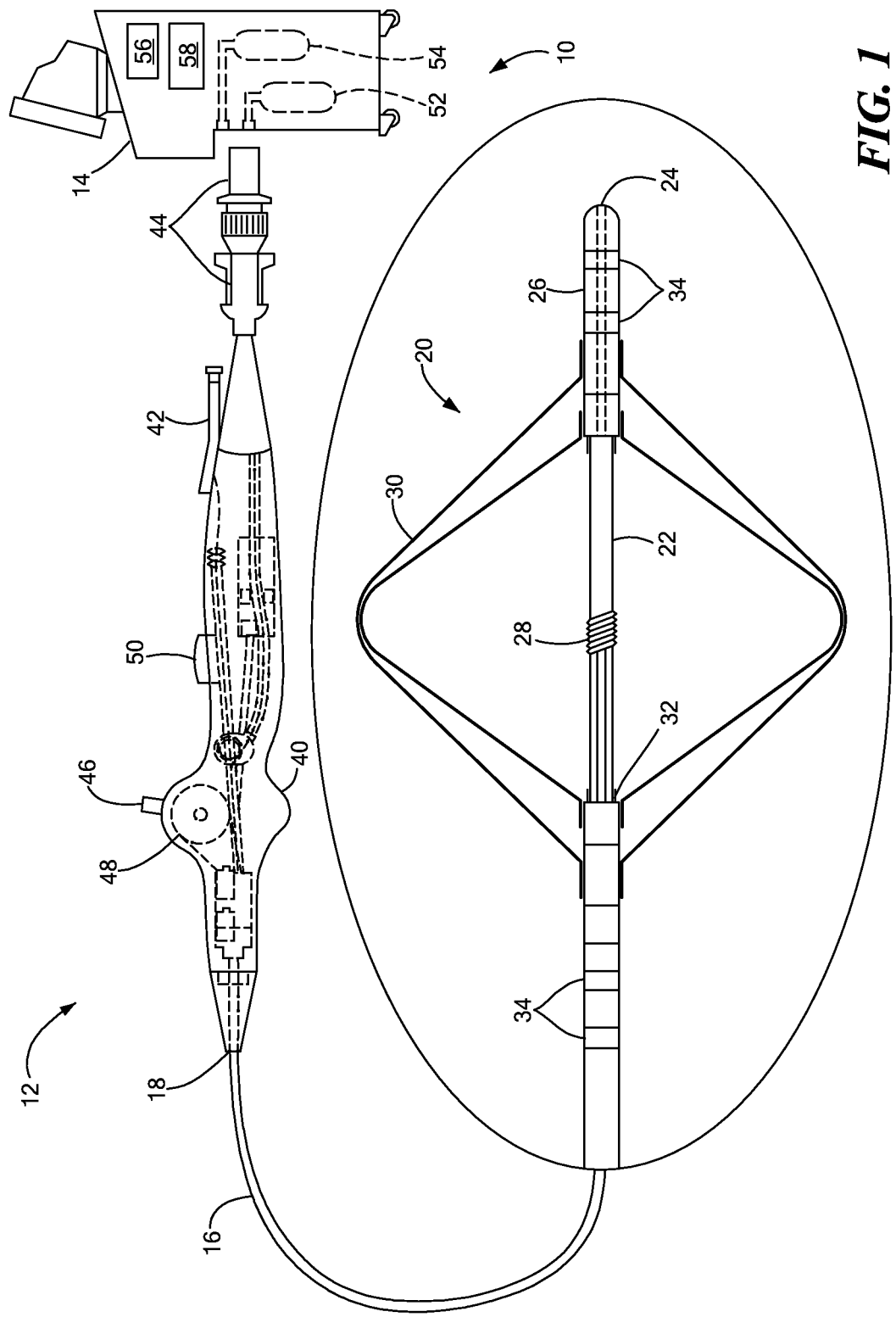
FIG. 1 is an illustration of an example of a medical system constructed in accordance with the principles of the present invention.

The present invention advantageously provides a system and methods of use thereof for assessing tissue contact, lesion quality and depth, and other characteristics of ablated or thermally-treated tissue to determine the characteristics and resulting efficacy of the treatment. Referring now to the drawing figures in which like reference designations refer to like elements, an embodiment of a medical system constructed in accordance with principles of the present invention is shown in FIG. 1 and generally designated as "10." The system 10 generally includes a medical device 12 that may be coupled to a control unit 14 or operating console. The medical device 12 may generally include one or more diagnostic or treatment regions for energetic, therapeutic and/or investigatory interaction between the medical device 12 and a treatment site. The treatment region(s) may deliver, for example, cryogenic therapy, radiofrequency energy, or other energetic transfer with a tissue area in proximity to the treatment region(s), including cardiac tissue.

Now referring to FIG. 1, the medical device 12 may include an elongate body 16 passable through a patient's vasculature and/or proximate to a tissue region for diagnosis or treatment, such as a catheter, sheath, or intravascular introducer. The elongate body 16 may define a proximal portion 18 and a distal portion 20, and may further include one or more lumens disposed within the elongate body 16 thereby providing mechanical, electrical, and/or fluid communication between the proximal portion of the elongate body 16 and the distal portion of the elongate body 16, as discussed in more detail below.

The medical device 12 may include a shaft 22 at least partially disposed within a portion of the elongate body 16. The shaft 22 may extend or otherwise protrude from a distal end of the elongate body 16, and may be movable with respect to the elongate body 16 in longitudinal and rotational directions. That is, the shaft 22 may be slidably and/or rotatably moveable with respect to the elongate body 16. The shaft 22 may further define a lumen 24 therein for the introduction and passage of a guide wire. The shaft 22 may include or otherwise be coupled to a distal tip 26 that defines an opening and passage therethrough for the guide wire.

The medical device 12 may further include a fluid delivery conduit 28 traversing at least a portion of the elongate body and towards the distal portion. The delivery conduit 28 may be coupled to or otherwise extend from the distal portion of the elongate body 16, and may further be coupled to the shaft 22 and/or distal tip of the medical device 12. The fluid delivery conduit 28 may define a lumen therein for the passage or delivery of a fluid from the proximal portion of the elongate body 16 and/or the control unit 14 to the distal portion and/or treatment region of the medical device 12. The fluid delivery conduit 28 may further include one or more apertures or openings therein, to provide for the dispersion or directed ejection of fluid from the lumen to an environment exterior to the fluid delivery conduit 28.

The medical device 12 may further include one or more expandable elements 30 at the distal portion of the elongate body 16. The expandable element 30 may be coupled to a portion of the elongate body 16 and also coupled to a portion of the shaft 22 and/or distal tip 26 to contain a portion of the fluid delivery conduit 28 therein. The expandable element 30 defines an interior chamber or region that contains coolant or fluid dispersed from the fluid delivery conduit 28, and may be in fluid communication with an exhaust lumen 32 defined by or included in the elongate body 16 for the removal of dispersed coolant from the interior of the expandable element 30. The expandable element 30 may further include one or more material layers providing for puncture resistance, radiopacity, or the like.

Figure 2:
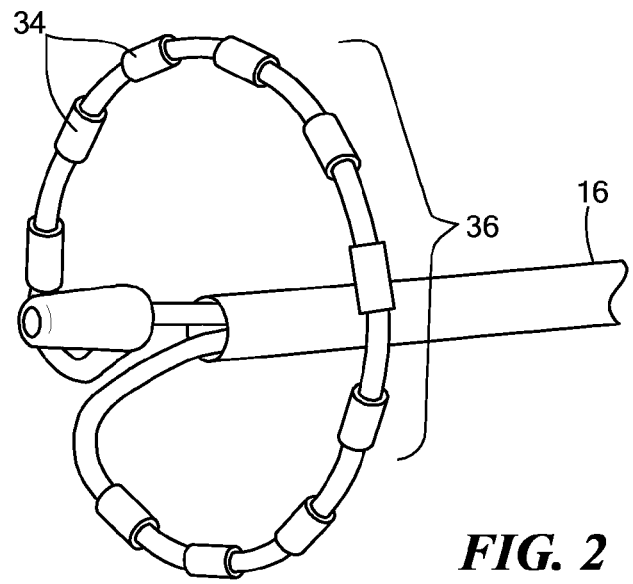
FIG. 2 is an illustration of an example of a medical device assembly constructed in accordance with the principles of the present invention.
Figure 3:
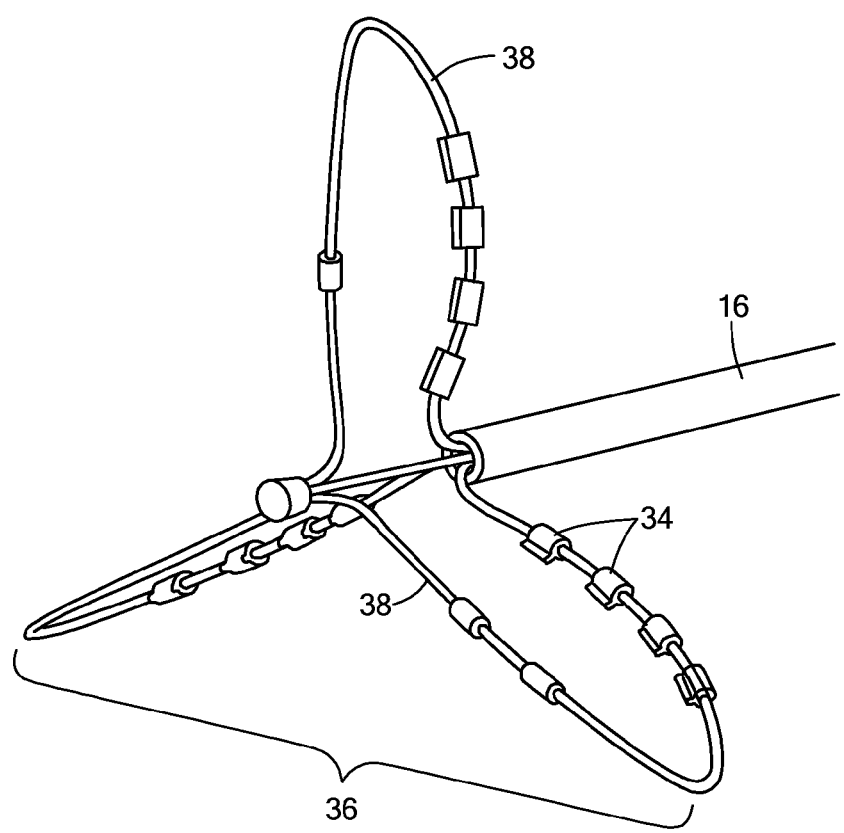
FIG. 3 is another illustration of an example of a medical device assembly constructed in accordance with the principles of the present invention.
Figure 4:
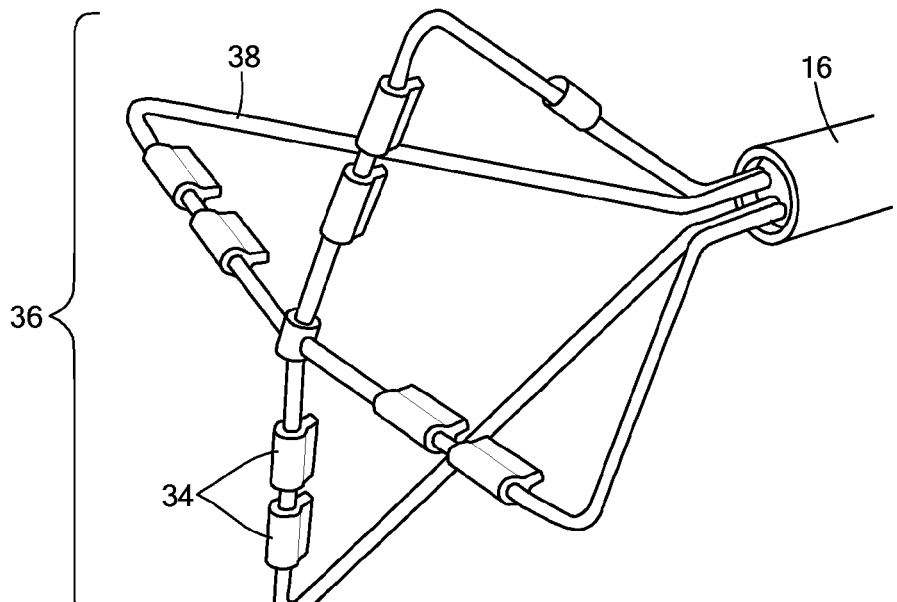
FIG. 4 is still another illustration of an example of a medical device assembly constructed in accordance with the principles of the present invention.
Figure 5:
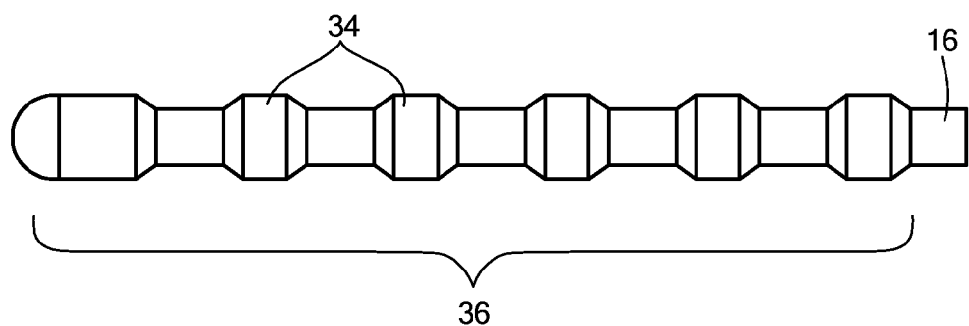
FIG. 5 is yet another illustration of an example of a medical device assembly constructed in accordance with the principles of the present invention.

The medical device 12 may further include one or more electrically-conductive segments or electrodes 34 positioned on or about the elongate body for conveying an electrical signal, current, or voltage to a designated tissue region and/or for measuring, recording, or otherwise assessing one or more electrical properties or characteristics of surrounding tissue. The electrodes 34 may be configured in a myriad of different geometric configurations or controllably deployable shapes, and may also vary in number to suit a particular application, targeted tissue structure or physiological feature. For example, as shown in FIG. 1, the electrodes 34 may include a first pair proximate to the expandable element and a second electrode pair distal to the expandable element. Alternative electrode configurations of the medical device 12 are illustrated in FIGS. 2-5. FIG. 2 includes an electrode array 36 configurable into a looped or substantially circular configuration. The electrode array 36 in FIG. 3 includes a plurality of arms 38, with the electrodes 34 positioned in a proximal-facing direction or orientation on the arms 38. FIG. 4 also includes a plurality of extendable or deployable arms 38 having a plurality of electrodes 34 in a square-like or "X"-shaped configuration. Turning to FIG. 5, a plurality of electrodes 34 are shown in a substantially linear array 36 extending along a portion of the elongate body 16 of the medical device 12. Additional details related to the configurations, manipulation, and exemplary uses of the electrode configurations shown in FIGS. 2-5 are provided in U.S. patent application Ser. No. 12/116,753, filed on May 7, 2008, entitled "Ablation Therapy System and Method for Treating Continuous Atrial Fibrillation," the entirety of which is hereby incorporated by reference.

Each electrode 34 may be electrically coupled to an output portion of a radiofrequency signal generator, and each electrode 34 may also include a sensor, such as a thermocouple, an electrical conductivity sensor, a spectrometer, a pressure sensor, a fluid flow sensor, a pH sensor, and/or a thermal sensor (not shown) coupled to or in communication with the electrodes. The sensors may also be in communication with a feedback portion of the control unit 14 to trigger or actuate changes in operation when predetermined sequences, properties, or measurements are attained or exceeded.

Referring again to FIG. 1, the medical device 12 may include a handle 40 coupled to the proximal portion of the elongate body 16. The handle 40 can include circuitry for identification and/or use in controlling of the medical device 12 or another component of the system. Additionally, the handle 40 may be provided with a fitting 42 for receiving a guide wire that may be passed into the guide wire lumen 24. The handle 40 may also include connectors 44 that are matable to the control unit 14 to establish communication between the medical device 12 and one or more components or portions of the control unit 14.

The handle 40 may also include one or more actuation or control features that allow a user to control, deflect, steer, or otherwise manipulate a distal portion of the medical device 12 from the proximal portion of the medical device 12. For example, the handle 40 may include one or more components such as a lever or knob 46 for manipulating the elongate body 16 and/or additional components of the medical device 12. For example, a pull wire 48 with a proximal end and a distal end may have its distal end anchored to the elongate body 16 at or near the distal portion 20. The proximal end of the pull wire 48 may be anchored to an element such as a cam in communication with and responsive to the lever 46. The medical device 12 may include an actuator element 50 that is movably coupled to the proximal portion of the elongate body 16 and/or the handle 40 for the manipulation and movement of a portion of the medical device 12, such as the shaft 22, and/or one or more portions of the electrode assemblies described above, for example.

The system 10 may include one or more treatment sources coupled to the medical device for use in an operative procedure, such as tissue ablation, for example. The control unit 14 may include a fluid supply 52 including a coolant, cryogenic refrigerant, or the like, an exhaust or scavenging system (not shown) for recovering or venting expended fluid for re-use or disposal, as well as various control mechanisms. In addition to providing an exhaust function for the fluid or coolant supply 52, the control unit 14 may also include pumps, valves, controllers or the like to recover and/or re-circulate fluid delivered to the handle 40, the elongate body 16, and/or the fluid pathways of the medical device 12. A vacuum pump 54 in the control unit 14 may create a low-pressure environment in one or more conduits within the medical device 12 so that fluid is drawn into the conduit(s)/lumen(s) of the elongate body 16, away from the distal portion 20 and towards the proximal portion 18 of the elongate body 16.

The control 14 unit may include a radiofrequency generator or power source 56 as a treatment or diagnostic mechanism in communication with the electrodes 34 of the medical device 12. The radiofrequency generator 56 may have a plurality of output channels, with each channel coupled to an individual electrode 34. The radiofrequency generator 56 may be operable in one or more modes of operation, including for example: (i) bipolar energy delivery between at least two electrodes on the medical device within a patient's body, (ii) monopolar or unipolar energy delivery to one or more of the electrodes 34 on the medical device 12 within a patient's body and through a patient return or ground electrode (not shown) spaced apart from the electrodes 34 of the medical device 14, such as on a patient's skin for example, and (iii) a combination of the monopolar and bipolar modes.

The system 10 may further include one or more sensors to monitor the operating parameters throughout the system, including for example, pressure, temperature, flow rates, volume, power delivery, impedance, or the like in the control unit 14 and/or the medical device 12, in addition to monitoring, recording or otherwise conveying measurements or conditions within the medical device 12 or the ambient environment at the distal portion of the medical device 12. The sensor(s) may be in communication with the control unit 14 for initiating or triggering one or more alerts or therapeutic delivery modifications during operation of the medical device 12. One or more valves, controllers, or the like may be in communication with the sensor(s) to provide for the controlled dispersion or circulation of fluid through the lumens/fluid paths of the medical device 12. Such valves, controllers, or the like may be located in a portion of the medical device 12 and/or in the control unit 14.

The control unit 14 may include one or more controllers, processors, and/or software modules containing instructions or algorithms to provide for the automated operation and performance of the features, sequences, calculations, or procedures described herein. For example, the control unit 14 may include an impedance measurement module or signal processing unit 58 to measure one or more impedance characteristics between the electrodes of the medical device. An excitation current may be applied between one or more of the electrodes 34 on the medical device 12 and/or a patient return electrode, and the resulting impedance may be measured, as described in more detail below. Excitation and the resulting measurements for impedance parameters may continue or otherwise be repeated until impedance measurements are calculated for various combinations of electrodes during and/or after a designated procedure.

Figure 6:
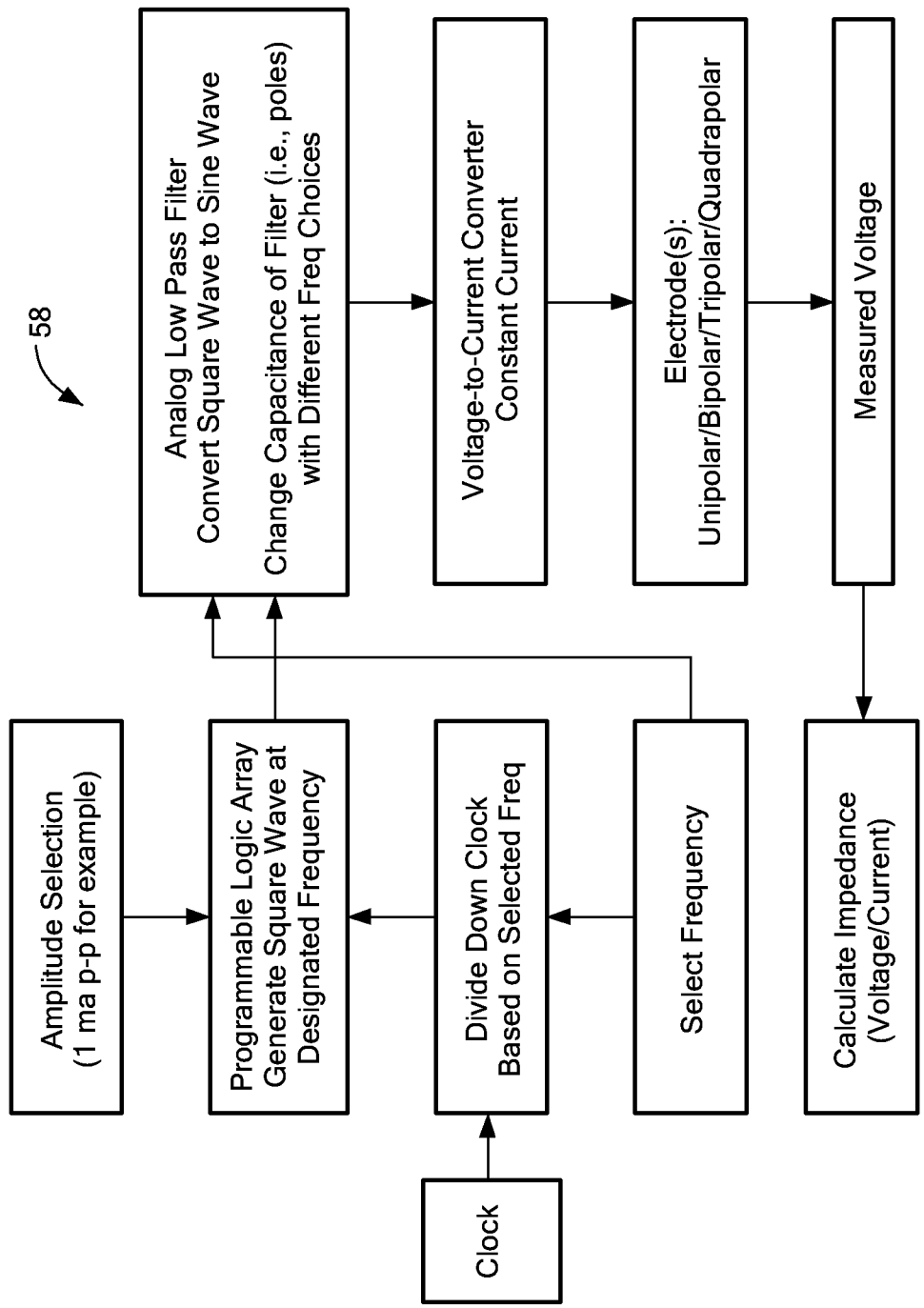
FIG. 6 is a flow chart illustrating an exemplary method of use of a medical system in accordance with the principles of the present invention.

Now referring to FIG. 6, an illustrative block diagram is presented for an exemplary implementation of the impedance measurement module 58 of the control unit 14. The module 58 may generally include a frequency selection input. The designated frequency may be divided down based on a frequency of an internal clock, which may be used by a programmable logic array to generate a square wave at a desired frequency with a set amplitude. The output of the programmable logic array may proceed to a low pass filter which converts the square-wave to a sine wave. The capacitance of the filter may be changed depending upon the selected frequency. The output of the low pass filter may proceed to a voltage-to-current converter which in turn, directs a substantially constant current output to one or more of the electrodes of the medical device. The output to the electrodes may be multiplexed in a variety of different modes, including unipolar (e.g., from one or more electrodes to a patient return electrode); bipolar (e.g., between electrodes on the medical device); tripolar (e.g., direct current from a first to second electrode, and measure a voltage between the second and a third electrode); and/or quadrapolar (direct current to first and second electrodes; measure a voltage between a third and fourth electrode) operations. The electrodes may also be operated in a combination of such modes, including, for example, delivering current between a plurality of different electrodes in varying phases and measuring voltages between differing pairs of electrodes in unipolar and bipolar modalities, and calculating the resulting resistances and phase values. The measured values obtained from the various modes of operations may then be used to calculate an impedance characteristic (e.g., magnitude and/or phase).

In an exemplary method of use, the system may be used to treat tissue and to assess the resulting efficacy of the treatment. In particular, the medical device may be used to assess contact with the targeted tissue, thermally treat tissue using cryogenic and/or radiofrequency energy provided by the control unit, and then provide measurements or indications of the efficacy of the treatment. The thermal treatment may include ablating one or more portions of a targeted tissue area or region, such as in the heart. Before, during and after completion of the desired thermal treatment, the medical device and control unit may be used to assess one or more characteristics of the treated tissue regions. The electrodes of the medical device may be used to measure one or more impedance characteristics of the treated tissue as an indication of the rate of tissue treatment, treatment continuity, and/or treatment depth. The measured characteristics may further be used post-treatment in a secondary or follow-up procedure to locate and assess previously treated tissue regions.

As used herein, the term impedance refers to the generally accepted definition of the term: a complex ratio of sinusoidal voltage to current in an electric circuit or component, except that as used herein, impedance shall apply to any region or space through which some electrical field is applied and current flows. The impedance, Z, may be expressed as a complex number, $Z=R+jX$, wherein R is the resistance in real number ohms, X is the reactance in imaginary number ohms, and j is a multiplier that is the positive square root of negative one (−1). Impedance may also be expressed in polar form as $Z=|Z| e^{j\theta}$, where $|Z|$ is the magnitude (e.g., the ratio of the voltage difference amplitude to the current amplitude), θ is the phase difference between voltage and current, and j is the imaginary unit.

Figure 7:
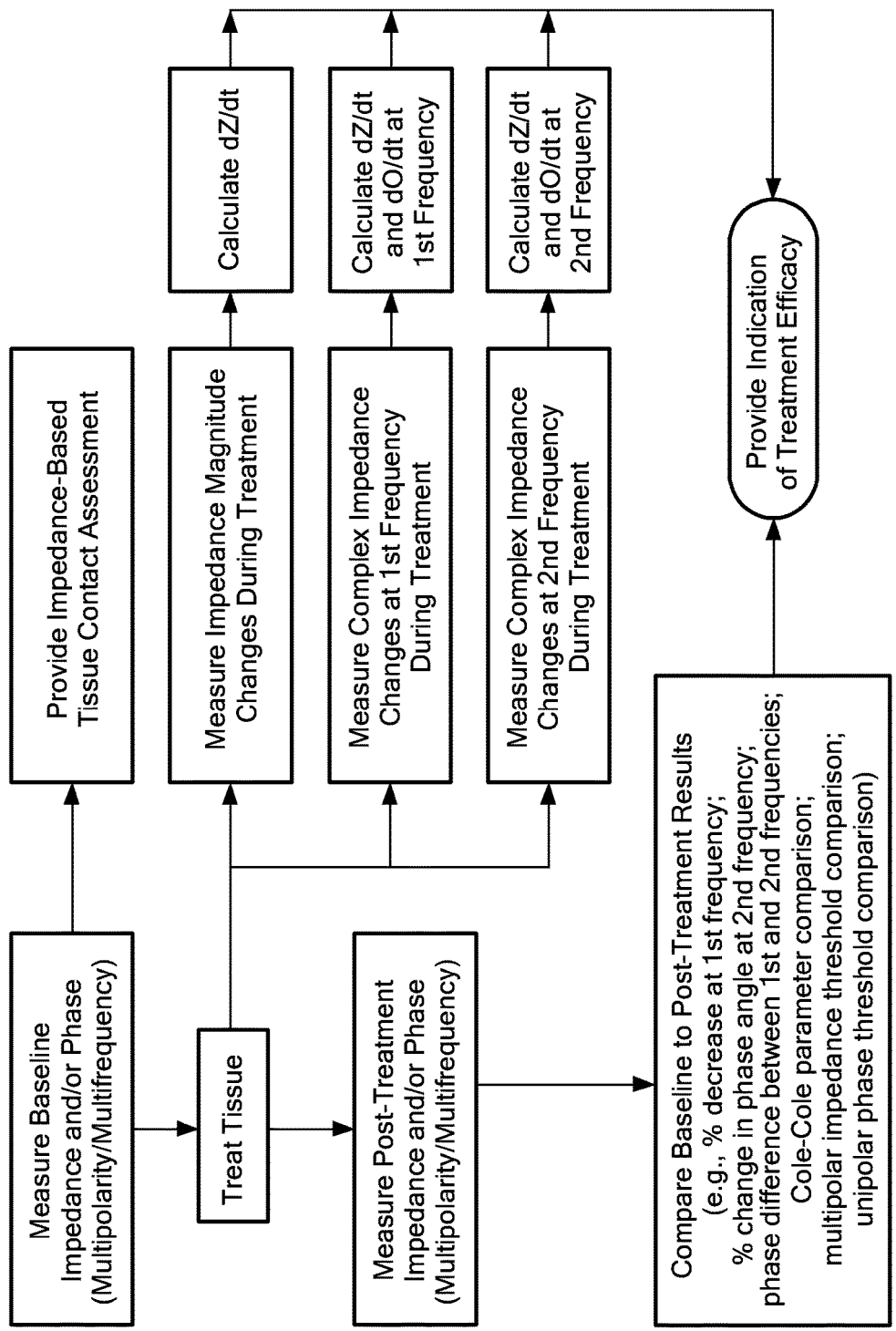
FIG. 7 is a flow chart illustrating another exemplary method of use of a medical system in accordance with the principles of the present invention.

Now turning to the flow chart of FIG. 7, an exemplary method is shown using the system 10. Primarily, the distal end of the medical device may be positioned proximate to a tissue region or structure to be treated. The positioning may include placing the electrode(s) of the medical device into contact with the targeted tissue. Once in a desired position, the electrodes may be used to obtain a series of impedance measurements to establish a pre-operative baseline and/or to assess the contact between the medical device and the targeted tissue. The impedance measurements may be taken with the electrodes of the medical device and processed by one or more components of the control unit.

The baseline impedance measurements may include both multi-polarity and multi-frequency measurements and combinations thereof. For example, impedance characteristics (including both impedance magnitude and phase, for example) may be measured in both bipolar (e.g., between electrodes on the medical device) and unipolar modes (e.g., between one or more of the electrodes on the medical device and a return electrode spaced from the medical device) of operation. Moreover, the series of measurements or assessments may be made at a first frequency or frequency range, while a second series of measurements may be made at a second frequency or frequency range. The first frequency range may include radiofrequencies of approximately 10 kHz or less, while the second frequency range may include radiofrequencies of approximately 200 kHz or greater. In a specific example, baseline impedance measurements may include obtaining both magnitude and phase measurements in unipolar operation at both a lower frequency range and a higher frequency range. The measurements may further include obtaining bipolar impedance magnitude and phase measurements at two distinct frequency settings or ranges.

The change in phase may be measured and/or calculated in several different ways. For example, the phase difference may be obtained by identifying the time of the peak of the measured voltage and comparing it to the time of a known peak from a generated current sine wave. Alternatively, the phase delay may be measured by gaining the measured voltage signal to create a square wave. The created square wave signal can then be subtracted from the original current square-wave signal as converted to a voltage, and the resultant pulse width can be measured implementing a timer or a microcontroller in the control unit, for example. The change in phase may also be determined by gaining the measured voltage signal and the generated current sine wave as converted to a voltage. These two signals can then be subtracted, and the resultant pulse width can then be measured to obtain the phase difference.

Of note, the measurements described herein may be obtained through direct sensing or measuring of a property or characteristic (e.g., impedance, resistance, etc.) between two or more electrodes, or may be obtained through calculations derived from a subset or direct measurements. For example, to obtain multiple impedance measurements between various combinations of existing electrodes, a plurality of bipolar and unipolar measurements may be taken, while calculating remaining values between other combinations of electrodes using matrix math or other computational algorithm. An example may include connecting a plurality of electrodes to the ground or patient electrode, and taking unipolar impedance measurements simultaneously between each electrode and the ground electrode. Subsequently, phase-varied currents may be sent to electrodes of the plurality to combined unipolar and bipolar conduction, e.g., establish a current path between a first electrode and the ground electrode at a 0 degree phase angle; subject a second electrode to a current 180 degrees out of phase with the current to electrode 1; send a 0 degree phase current to a third electrode, and subject a fourth electrode to a 180 degree phase-varied current. Measurements of the voltage between the first electrode and the ground electrode (unipolar); the second electrode and the ground electrode (unipolar); and between the first and second electrodes (bipolar) may then be taken. The resulting voltage, impedance, resistance, and/or other characteristics between combinations of the four electrodes can then be calculated using matrix math with the known measurements.

Figure 8:
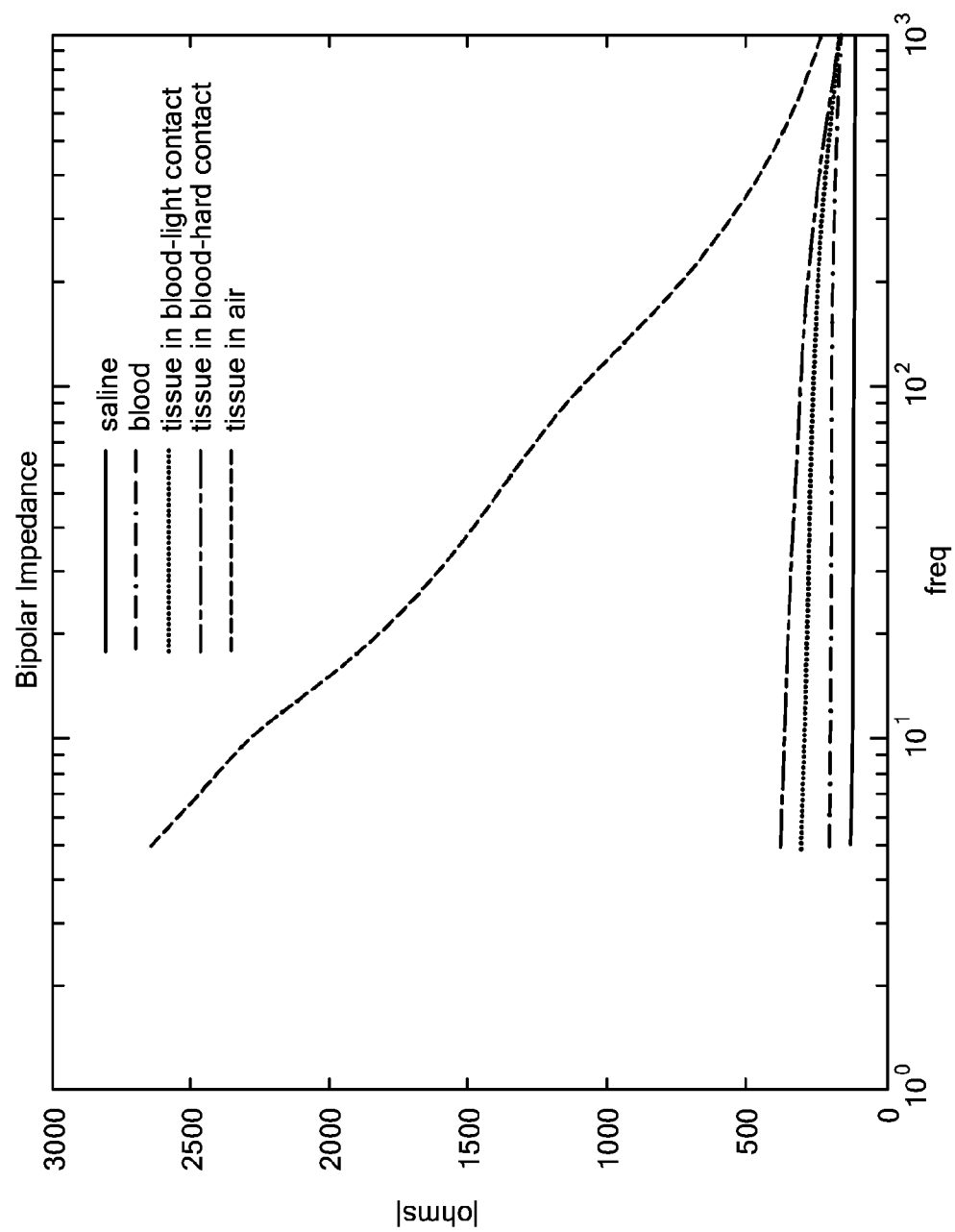
FIG. 8 is a graph of bipolar impedance values measured across a range of frequencies for varied contact situations for a medical device.
Figure 9:
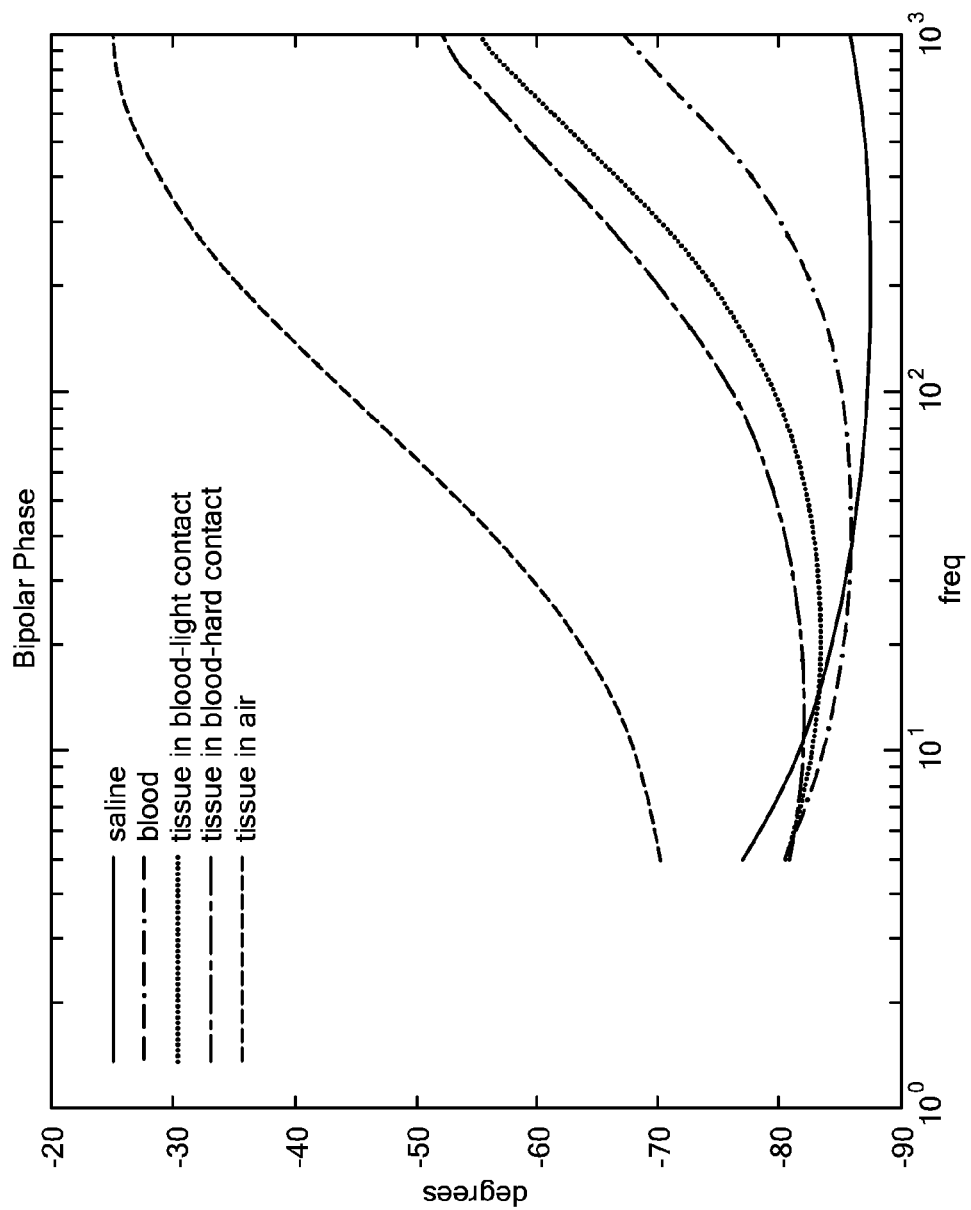
FIG. 9 is a graph of bipolar impedance phases measured across a range of frequencies for varied contact situations for a medical device.
Figure 10:
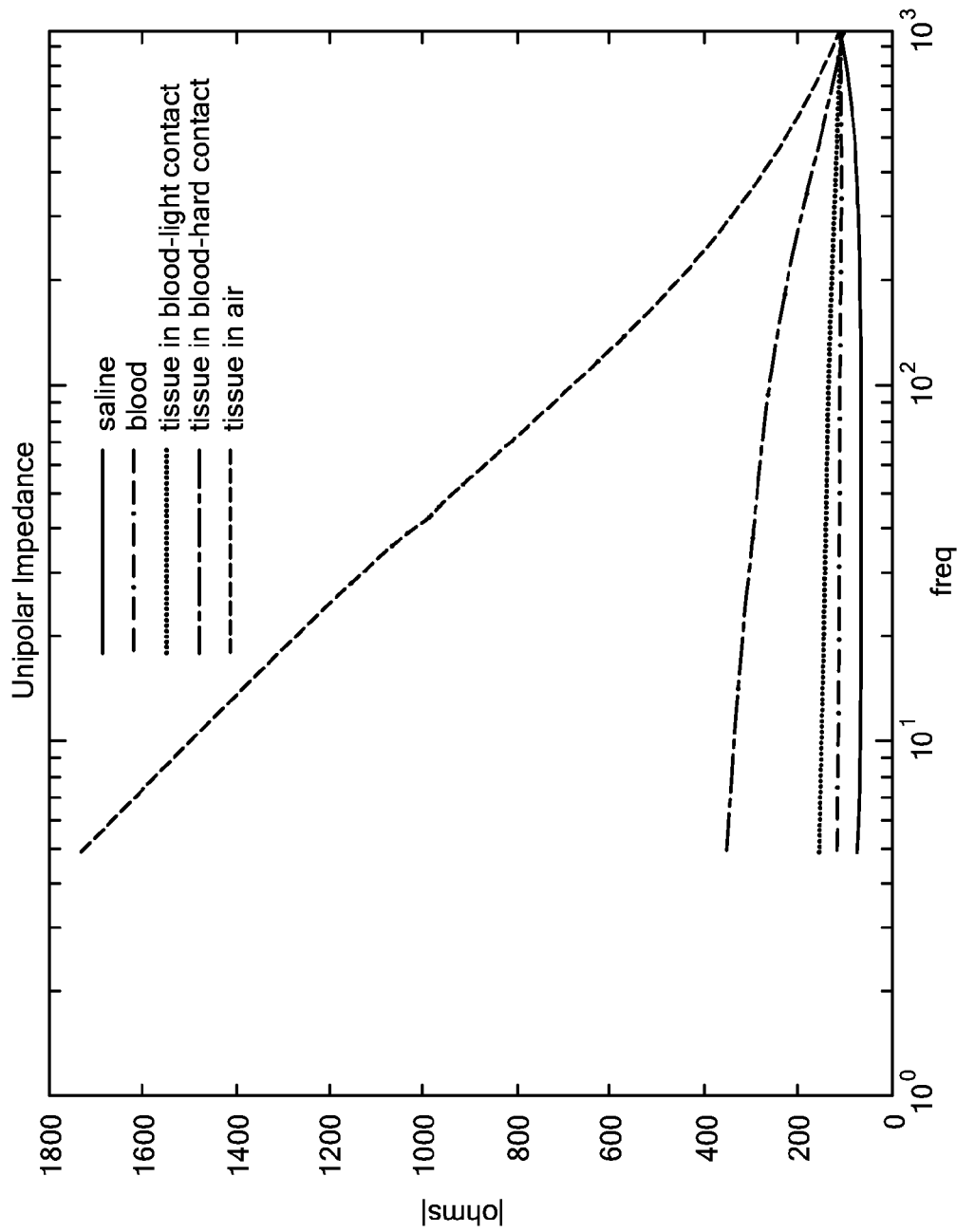
FIG. 10 is a graph of unipolar impedance values measured across a range of frequencies for varied contact situations for a medical device.
Figure 11:
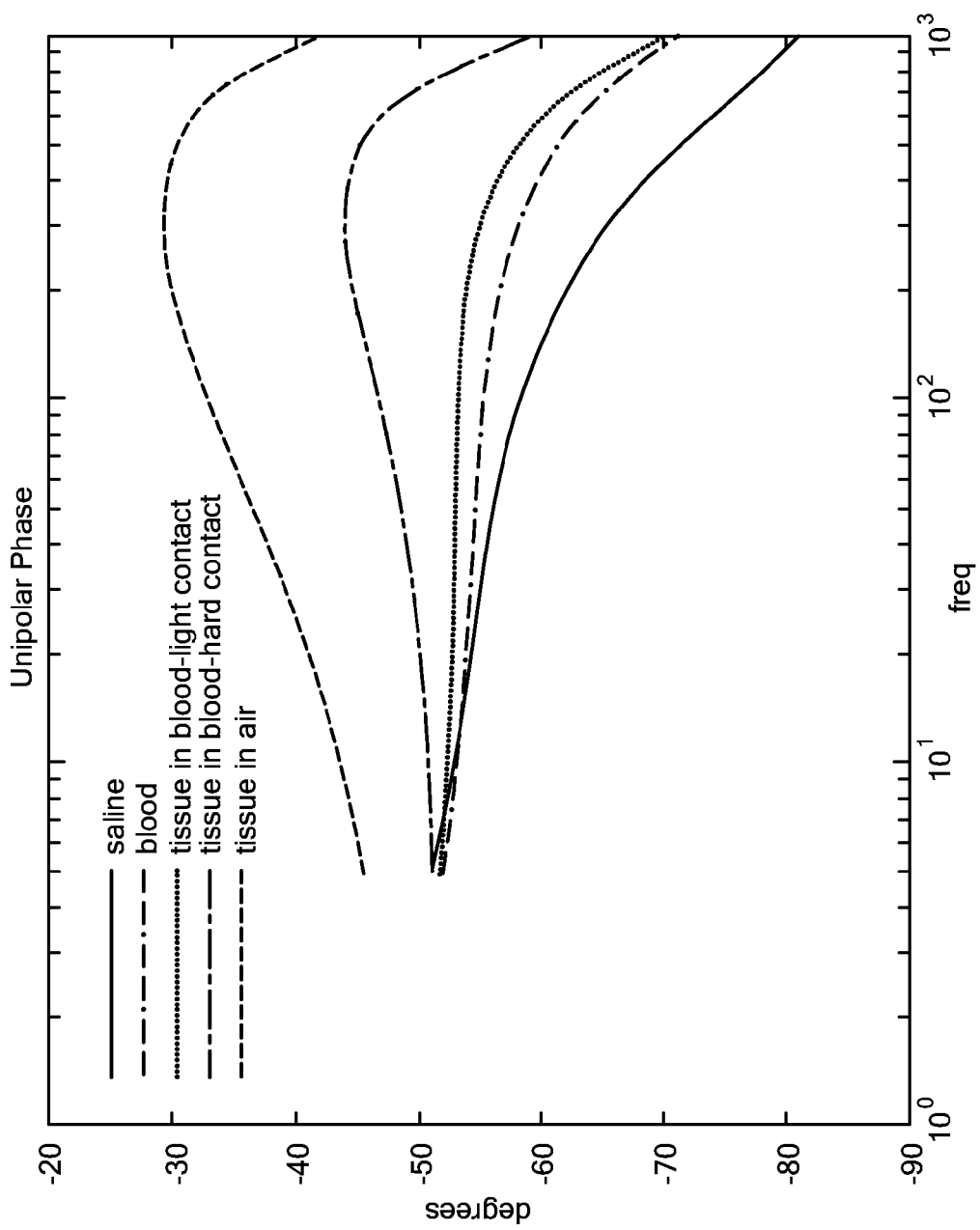
FIG. 11 is a graph of unipolar impedance phases measured across a range of frequencies for varied contact situations for a medical device.

Upon obtaining the baseline measurements of impedance magnitudes and phases, the obtained information may be processed to provide an indication of contact between the electrodes of the medical device and the targeted tissue. For example, as shown in FIG. 8, bipolar impedance values measured at varying levels of contact have a significant divergence at lower frequencies as compared to higher frequencies. The obtained measurements can thus be compared to predetermined thresholds or values to assess whether the medical device has light contact with the targeted tissue, strong contact, and/or is only in contact with blood flow or a fluid stream around the device. Turning now to FIG. 9, bipolar phase angle differences measured at varying levels of contact have a significant divergence at higher frequencies as compared to lower frequencies. FIG. 10 illustrates the difference in unipolar impedance values at lower frequencies depending on the contact level between the medical device and the targeted tissue, while unipolar phase difference measurements at higher frequencies also can provide an indication of contact assessment, as shown in FIG. 11. One or more of the multi-polarity, multi-frequency impedance and phase difference measurements can thus provide an indication or assessment of the contact of the medical device to an end user or physician. Depending on the obtained measurements and indications of effective contact, the medical device can be maneuvered or otherwise repositioned until a desired contact level is attained as reflected by one or more series of impedance measurements, repeated as necessary to obtain a desired contact for subsequent treatment.

Once the desired contact has been achieved and/or the baseline impedance characteristics have been measured and/or recorded, the medical device may be used to thermally treat the targeted tissue area. The thermal treatment may include, for example, circulating a coolant from the control unit to the distal end of the device, which may include the expandable element, for example. The treatment may include the delivery of ablative radiofrequency energy to the electrodes of the device. Treatment may also include a combination of cryogenic and radiofrequency operation either simultaneously or sequentially. During the thermal treatment, a plurality of impedance measurements may continue to be taken. For example, the electrodes may be used to measure magnitudes of impedance changes during the thermal treatment at a first frequency, such as the frequency used to ablate the tissue (such as between approximately 400 to 500 kHz, for example). The use of the electrodes to measure these characteristics during the treatment may occur during an "off" period of a duty cycle of delivered radiofrequency energy to minimize the disruption of the actual thermal treatment. The plurality of measurements may also include recording or measuring complex impedance changes of both magnitude and phase at a first, lower frequency range, as well as recording or measuring complex impedance changes of both magnitude and phase at a second, higher frequency range. The plurality of measurements may be used to calculate or process a rate of change of the impedance over time, a rate of change of impedance magnitude at a first frequency over time, a rate of change of impedance phase at a first frequency over time, a rate of change of impedance magnitude at a second frequency over time and/or a rate of change of impedance phase at a second frequency over time. The rates of change obtained from the plurality of measurements provide an indication of how fast (or slow) the targeted tissue is freezing, or heating. The rates of change can be compared to predefined or established clinical values for effective thermal treatment and thus provide the basis for an assessment of the ongoing efficacy of the thermal treatment, and can further be used to modify one or more treatment delivery parameters (such as target temperature, fluid flow, power delivery, etc.) in the operation of the medical device and/or terminate operation altogether. In addition to the thermal tissue treatment methods, delivery of high voltage pulses can also be used to permanently create holes in treated cell membranes without the use of hyperthermy or hypothermy. This allows more latitude in performing impedance phase measurements between deliveries of high voltage pulses or between pulse trains, avoiding any impedance measurement artifacts introduced from tissue temperature changes. Such intra-procedural measurements allow for automated end point detection of the completion of the ablation.

Upon completion of the treatment procedure, one or more post-treatment impedance characteristics may be assessed or recorded. The post-treatment measurements may include impedance characteristics taken with similar parameters to the baseline impedance measurements described above. For example, the post-treatment impedance measurements may include both multi-polarity and multi-frequency measurements and combinations thereof. Impedance characteristics (including both impedance magnitude and phase, for example) may be measured in both bipolar and unipolar modes of operation. Moreover, the series of measurements or post-treatment assessments may be made at a first frequency or frequency range, while a second series of measurements may be made at a second frequency or frequency range. The first frequency range may include radiofrequencies of approximately 10 kHz or less, while the second frequency range may include radiofrequencies of approximately 200 kHz or greater. In a specific example, post-treatment impedance measurements may include obtaining both magnitude and phase measurements in unipolar operation at both a lower frequency range and a higher frequency range. The measurements may further include obtaining bipolar impedance magnitude and phase measurements at two distinct frequency settings or ranges.

Figure 12:
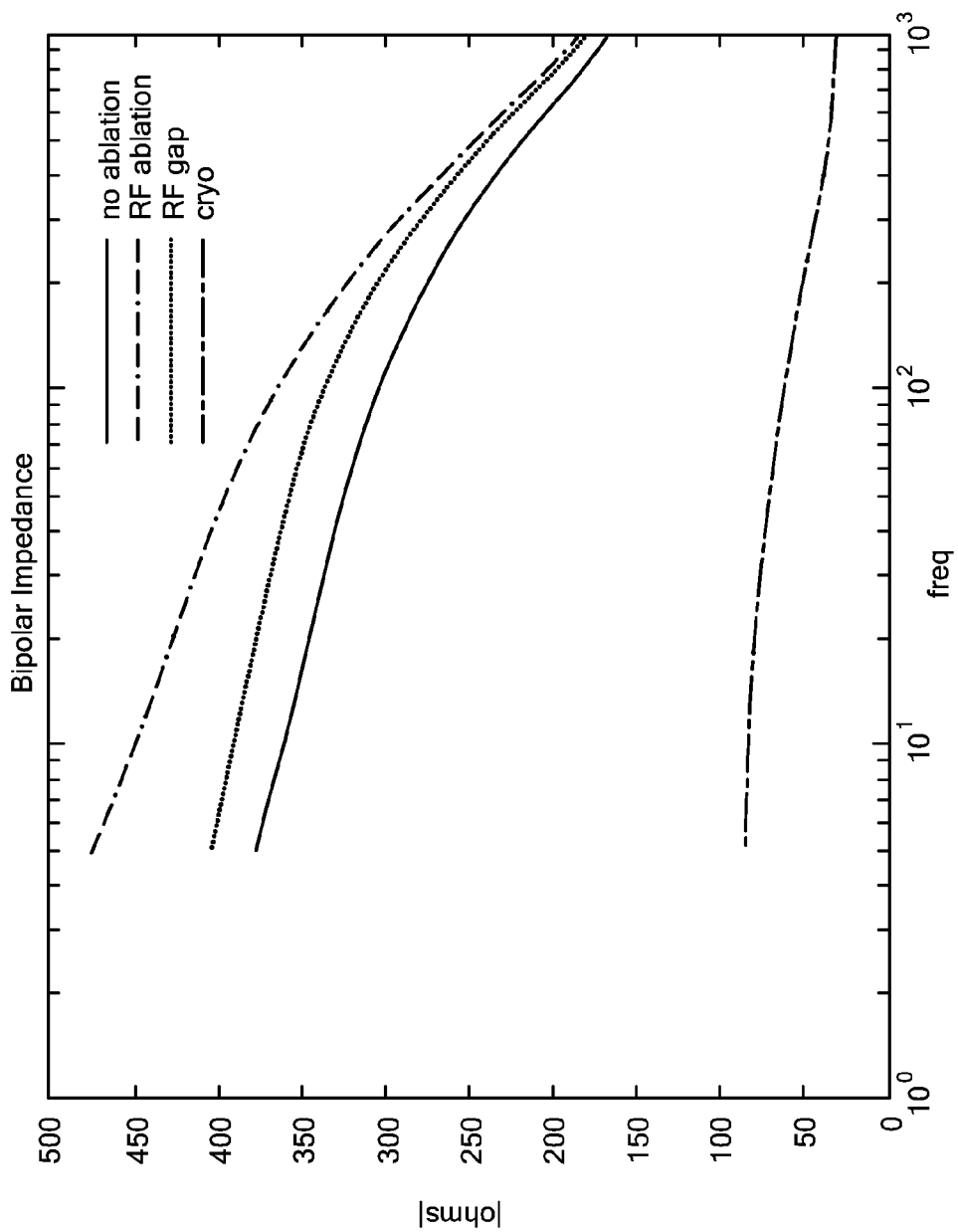
FIG. 12 is a graph of bipolar impedance values measured across a range of frequencies for varied tissue treatments.
Figure 13:
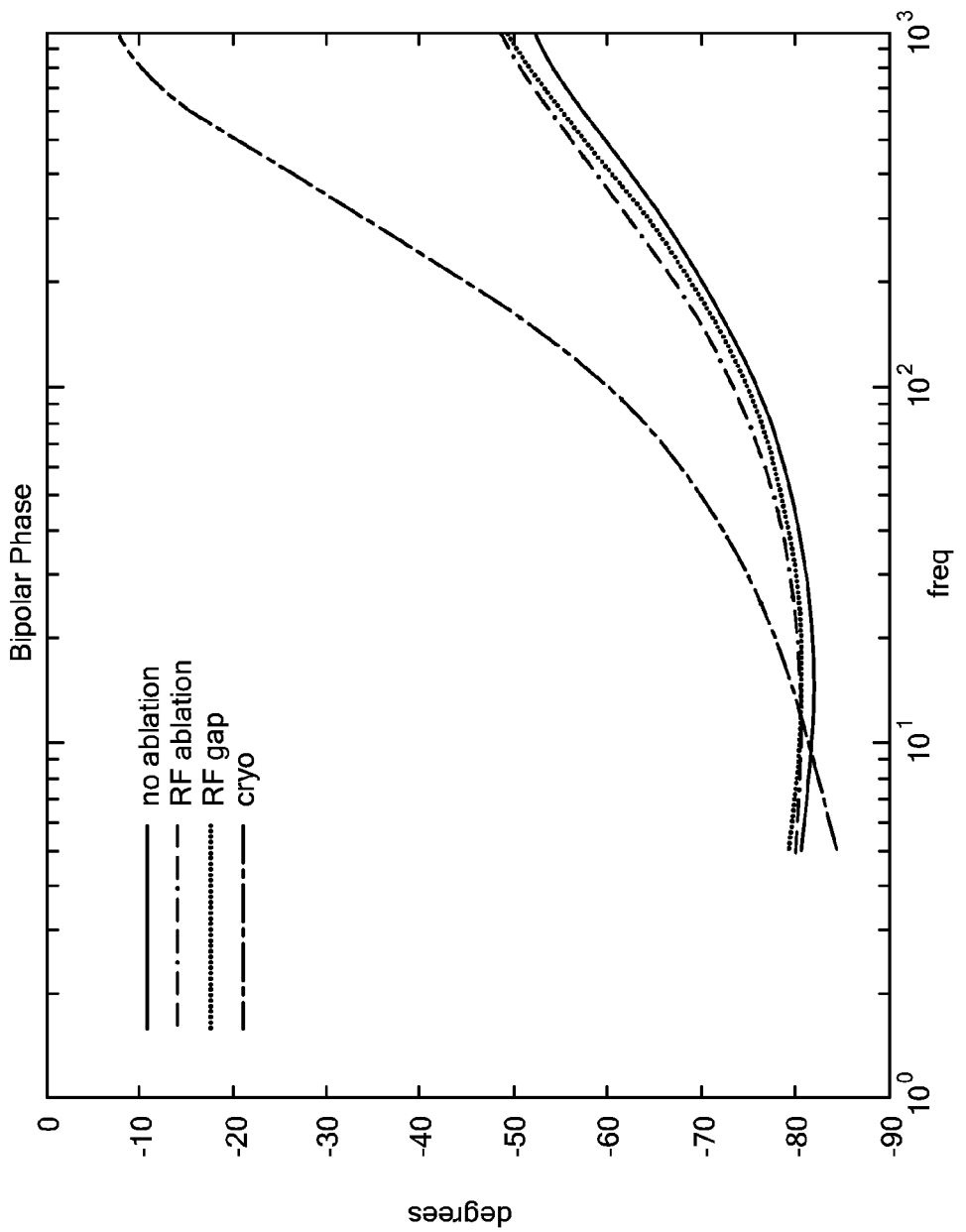
FIG. 13 is a graph of bipolar impedance phases measured across a range of frequencies for varied tissue treatments.
Figure 14:
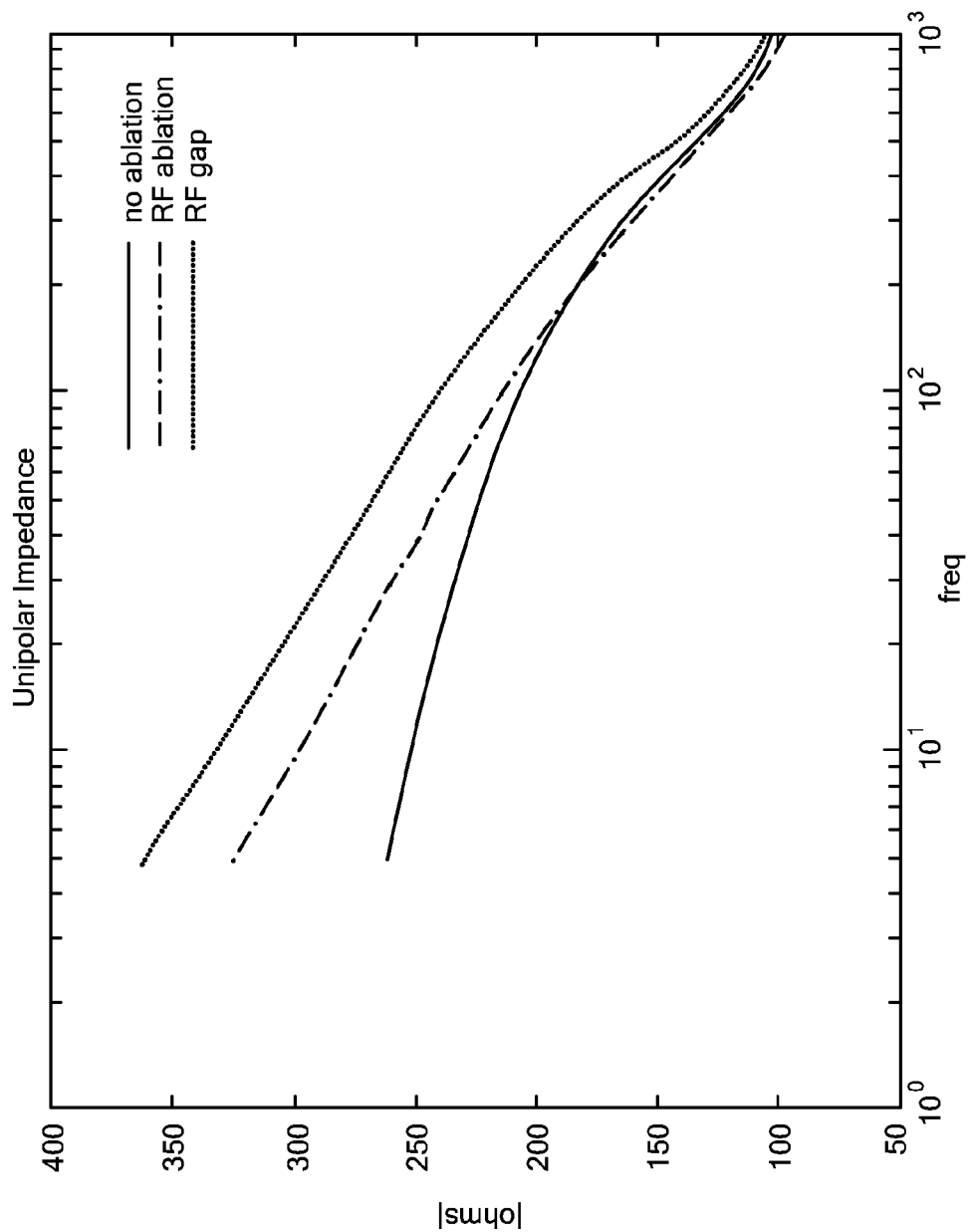
FIG. 14 is a graph of unipolar impedance values measured across a range of frequencies for varied tissue treatments.

The post-treatment measurements may be compared to the baseline measurements to form the basis as an indication of the efficacy of the treatment on the targeted tissue, or the post-treatment measurements may be used on their own to determine the resulting characteristics of the treated tissue segments, such as the treatment depth and/or continuity. For example, FIG. 12 shows that differences in bipolar impedance magnitude or values between (i) untreated tissue, (ii) tissue treated with radiofrequency energy, (iii) tissue partially treated or discontinuously treated with radiofrequency (e.g., the thermal segment has untreated gaps or spaces in it), and (iv) cryogenically-treated tissue are more significant in lower frequency ranges. FIG. 13 illustrates diverging values for bipolar phase difference at lower frequencies for (i) untreated tissue, (ii) tissue treated with radiofrequency energy, (iii) tissue partially treated or discontinuously treated with radiofrequency (e.g., the thermal segment has untreated gaps or spaced in it), and (iv) cryogenically-treated tissue. Unipolar impedance values can also be used to differentiate or assess the continuity of treated tissue, as shown in FIG. 14. The FIG. 14 graph shows differing unipolar impedance values at lower frequencies as indicative of whether a tissue segment is (i) untreated, (ii) treated with radiofrequency energy, or (iii) partially treated with radiofrequency energy.

Given the differences in impedance characteristics resulting from multi-polarity and multi-frequency measurements, the efficacy and modality (e.g., radiofrequency, cryogenic, etc.) of a treatment can be at least partially determined based on the post-treatment measurements of such impedance characteristics. Differences in multipolarity and/or multifrequency measurements may also be used to identify a region of tissue previously subjected to electroporation, which, similarly to radiofrequency and cryogenic treatment, changes the impedance and/or electrical characteristics of the affected cells evident in measurements of varying frequency and/or phase.

Comparing the baseline to the post-treatment measurements may include, for example, calculating a percentage decrease in the measured impedance values or magnitude at a first, lower frequency and/or calculating a percentage change in phase angle difference at a second, higher frequency range. The comparison may include, for example, the difference between impedance phase measured at a higher frequency and the measured phase at a lower frequency range. The comparison of baseline to post-treatment measurements may include assessing a change in Cole-Cole parameters. The post-treatment measurements may be compared to pre-established thresholds or values to determine whether the bipolar impedance values indicate a continuity of the thermally treated or ablated lesion or tissue segment. Predefined unipolar threshold comparisons of phase and/or magnitude may also be used to assess whether the post-treatment measurements indicate an effective depth of the treated segment. In addition to the examples above, different variations in the frequency and/or polarity of impedance magnitudes and/or phase may be utilized separately or in combination to provide a desired degree of specificity or accuracy for any given procedure.

Once the post-treatment measurements have been analyzed or otherwise processed with respect to the baseline measurements and/or predetermined, pre-established thresholds or values indicating efficacy, an indication of the efficacy of the treatment may be generated. The indication may include the assessment or inclusion of other treatment parameters, such as attained temperature, energy delivered, rate of change of temperature during treatment, etc. The processing and analysis may be performed by one or more components of the control unit 14, with the resulting analysis resulting in the generation of a user alert or indication of the analysis (e.g., a visual and/or audible indication).

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A medical system, comprising:
    a medical device positionable proximate a tissue site, the medical device comprising a plurality of electrodes and a patient return electrode operable to treat the tissue site; and
    a control unit in communication with the medical device, the control unit programmed to:
        deliver non-ablative radiofrequency energy at a first plurality of frequencies to the target tissue in a unipolar mode and a bipolar mode, wherein in the unipolar mode, the non-ablative radiofrequency energy is delivered between one electrode from the plurality of electrodes and the patient return electrode and in the bipolar mode, the non-ablative radiofrequency energy is delivered between two electrodes of the plurality of electrodes;
        receive baseline impedance characteristics at a first plurality of frequencies in both the unipolar and bipolar modes;
        deliver radiofrequency energy to the plurality of electrodes to ablate the target tissue;
        deliver non-ablative radiofrequency energy at a second plurality of frequencies to the target tissue in both the unipolar and bipolar modes;
        receive post-treatment impedance characteristics at the second plurality of frequencies in both the unipolar and bipolar modes;
        perform a comparison between the post-treatment impedance characteristics and the baseline impedance characteristics; and
        generate an indication of the efficacy of the ablation of the target tissue based at least in part on the comparison between the post-treatment and the baseline impedance characteristics.

2. The system of claim 1, wherein the baseline and the post-treatment impedance characteristics each includes at least one impedance magnitude value, and the comparison includes calculating a percentage difference between the at least one impedance magnitude value of the baseline and post-treatment impedance characteristics.

3. The system of claim 1, wherein the baseline and the post-treatment impedance characteristics each includes at least one impedance phase value, and the control unit is programmed to calculate a percentage difference between the at least one impedance phase value of the baseline and post-treatment impedance characteristics.

4. The system of claim 1, wherein the first plurality of frequencies are substantially the same as the second plurality of frequencies.

5. A medical system for assessing a tissue ablation treatment, comprising:
   a medical device positionable adjacent a target tissue, the medical device comprising a plurality of electrodes and a patient return electrode operable to treat the tissue site; and
   a control unit in communication with the medical device, the control unit programmed to:
      deliver non-ablative radiofrequency energy at a first frequency and a second frequency to the target tissue in both unipolar and bipolar modes, wherein in the unipolar mode, the non-ablative radiofrequency energy is delivered between one electrode from the plurality of electrodes and the patient return electrode and in the bipolar mode, the non-ablative radiofrequency energy is delivered between two electrodes of the plurality of electrodes;
      measure, in both the unipolar and bipolar modes, a baseline first impedance magnitude at the first frequency;
      measure, in both the unipolar and bipolar modes, a baseline first impedance phase at the second frequency;
      deliver radiofrequency energy to the plurality of electrodes to ablate at least a portion of the target tissue;
      deliver non-ablative radiofrequency energy at a third frequency and a fourth frequency to the target tissue in both the unipolar and bipolar modes,
      measure, in both the unipolar and bipolar modes, a post-ablation second impedance magnitude at the third frequency; and
      measure, in both the unipolar and bipolar modes, a post-ablation second impedance phase at the fourth frequency;
      perform a comparison between at least one of (i) the baseline first and post-ablation second impedance magnitudes and (ii) the baseline first and post-ablation second impedance phases; and
      provide an indication of the efficacy of the ablation of the target tissue based at least in part on the comparison.

6. The system of claim 5, wherein the medical device is configured to ablate the target tissue by the application of cryogenic energy, radiofrequency energy, or pulsed high voltage energy.

7. The system of claim 5, wherein the first frequency and the third frequency are substantially the same.

8. The system of claim 7, wherein the second frequency and the fourth frequency are substantially the same.

9. The system of claim 5, wherein the first frequency and the third frequency are each approximately 10 kHz or less.

10. The system of claim 9, wherein the second frequency and the fourth frequency are each approximately 200 kHz or more.

11. The system of claim 5, wherein the second frequency and the fourth frequency are each larger than the first and third frequencies.

12. The system of claim 5, wherein when the control unit compares at least one of (i) the baseline first impedance magnitude and the post-ablation second impedance magnitude and (ii) the baseline first impedance phase and the post-ablation second impedance phase, the control unit being programmed to calculate a percentage difference between the compared measurements.

13. The system of claim 5, wherein the control unit is further programmed to measure a plurality of impedance magnitudes during the ablation, and the control unit is further programmed to calculate a rate of change of the impedance magnitudes measured during the ablation.

14. The system of claim 5, wherein the control unit is further programmed to measure a plurality of impedance phases during the ablation, and the control unit is further programmed to calculate a rate of change of the impedance phases measured during the ablation.

15. The system of claim 5, wherein: the control unit is further programmed to:
   measure at least one of a plurality of impedance phases and a plurality of impedance magnitudes at the first frequency during the ablation;
   measure at least one of a plurality of impedance phases and a plurality of impedance magnitudes at the second frequency during the ablation;
   calculate a rate of change of the at least one of the plurality of impedance phases and a rate of change of the plurality of impedance magnitudes measured during the ablation at the first frequency; and
   calculate a rate of change of the at least one of the plurality of impedance phases and a rate of change of the plurality of impedance magnitudes measured during the ablation at the second frequency.

16. The system of claim 15, wherein the indication of the efficacy of the ablation is based at least in part on the calculated rates of change of the at least one of the plurality of impedance phases and the plurality of impedance magnitudes measured during the ablation at the first and second frequencies.

17. A system for assessing a tissue ablation treatment, the system comprising:
   a medical device positionable adjacent a tissue site, the medical device including a plurality of electrodes and a patient return electrode; and
   a control unit in communication with the medical device, the control unit programmed to:
      deliver non-ablative radiofrequency energy at a first plurality of frequencies to the tissue site in both unipolar mode and bipolar mode; wherein in the unipolar mode, the non-ablative radiofrequency energy is delivered between one electrode from the plurality of electrodes and the patient return electrode and in the bipolar mode, the non-ablative radiofrequency energy is delivered between two electrodes of the plurality of electrodes;
      obtain baseline impedance characteristics at the first plurality of frequencies in both the unipolar and bipolar modes;

deliver ablative radiofrequency energy to the tissue site at a first frequency in at least one of the unipolar mode and the bipolar mode;

obtain in-treatment impedance characteristics at the first frequency in the at least one of the unipolar mode and the bipolar mode;

deliver non-ablative radiofrequency energy at a second plurality of frequencies to the tissue site in both the unipolar and bipolar modes;

obtain post-treatment impedance characteristics at the second plurality of frequencies in both the unipolar and bipolar modes, the first frequency being different than at least one of the frequencies of the first and second plurality of frequencies; and perform a comparison between the post-treatment impedance characteristics obtained at the second plurality of frequencies in both the unipolar mode and the bipolar mode and the baseline impedance characteristics obtained at the first plurality of frequencies in both the unipolar mode and the bipolar mode; and generate an indication of the efficacy of the tissue ablation treatment based at least in part on the comparison.

18. The system of claim 17, wherein the control unit is further programmed to:

define an impedance characteristic threshold, and compare at least one of the baseline impedance characteristics obtained at the first plurality of frequencies in both the unipolar mode and the bipolar mode to the threshold and to compare at least one of the post-treatment impedance characteristics obtained at the second plurality of frequencies in both the unipolar mode and the bipolar mode to the impedance characteristic threshold.

19. The system of claim 17, wherein at least one of the baseline impedance characteristics obtained at the first plurality of frequencies in both the unipolar mode and the bipolar mode and the in-treatment impedance characteristics obtained at the second plurality of frequencies in both the unipolar mode and the bipolar mode includes an impedance phase.

20. The system of claim 17, wherein at least one of the baseline impedance characteristics obtained at the first plurality of frequencies in both the unipolar mode and the bipolar mode and the in-treatment impedance characteristics obtained at the second plurality of frequencies in both the unipolar mode and the bipolar mode includes an impedance magnitude.

* * * * *